US006147229A

United States Patent [19]

[11] Patent Number: 6,147,229

[45] Date of Patent: Nov. 14, 2000

Rasmussen et al.

[54] METHOD FOR PRODUCING MAGNESIUM FULVATE FROM HUMUS MATERIAL

[75] Inventors: Hans W. Rasmussen, St. George, Utah; Lawrence H. Allen, Hemet, Calif.

[73] Assignee: Electrolytes, Inc., Mesquite, Nev.

[21] Appl. No.: 09/472,044

[22] Filed: Dec. 27, 1999

[51] Int. Cl.[7] ............................ C07D 34/82; C07C 51/00

[52] U.S. Cl. ........................... 549/393; 549/392; 562/515

[58] Field of Search .................................... 549/392, 393; 562/515

[56] References Cited

U.S. PATENT DOCUMENTS

| | | |
|---|---|---|
| 4,459,149 | 7/1984 | Moran et al. . |
| 5,178,661 | 1/1993 | van der Watt et al. . |
| 5,213,692 | 5/1993 | Hjersted . |
| 5,302,180 | 4/1994 | Hjersted . |
| 5,411,569 | 5/1995 | Hjersted . |
| 5,626,881 | 5/1997 | Lown . |

*Primary Examiner*—Paul J. Killos
*Attorney, Agent, or Firm*—Blank, Rome, Comisky & McCauley LLP

[57] ABSTRACT

A method produces magnesium fulvate from naturally-occurring humus material, such as leonardite, or humic shales. The humus material containing solid fulvic acid and solid humic acid is mixed with water and sodium hydroxide for a first selected period of time to form a solution having a pH of approximately 10.0 thereby solubilizing the fulvic acid and the humic acid. The pH of the solution is reduced to approximately 4.5 and is maintained at the approximately pH 4.5 for second selected period of time thereby precipitating the humic acid as a solid while the fulvic acid remains in solution. The fulvic acid solution is separated from the solid humic acid. The pH of the fulvic acid solution is increased to approximately 13 with magnesium hydroxide thereby precipitating the solubilized fulvic acid as magnesium fulvate.

25 Claims, 1 Drawing Sheet

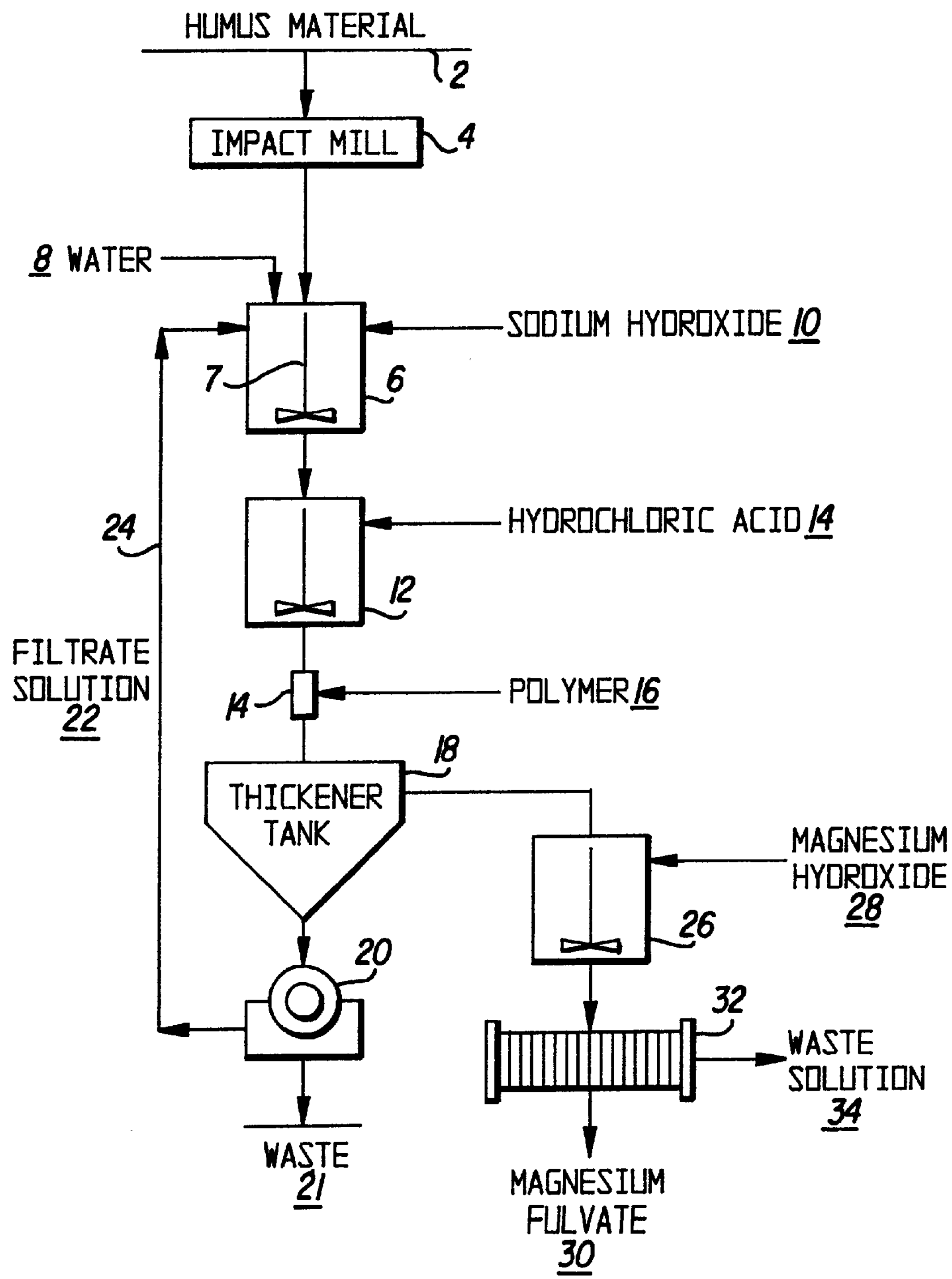
HUMUS MATERIAL
2
IMPACT MILL
4
8 WATER
SODIUM HYDROXIDE 10
7
6
24
HYDROCHLORIC ACID 14
12
FILTRATE SOLUTION 22
14
POLYMER 16
18
THICKENER TANK
MAGNESIUM HYDROXIDE 28
26
20
32
WASTE SOLUTION 34
WASTE 21
MAGNESIUM FULVATE 30

METHOD FOR PRODUCING MAGNESIUM FULVATE FROM HUMUS MATERIAL

FIELD OF THE INVENTION

The invention is directed to a method for producing magnesium fulvate from humus material.

BACKGROUND OF THE INVENTION

Leonardite and humus shales are sources of naturally-occurring humate material. Leonardite is a coal-like deposit having either a black, brown or blackish-brown color, containing 25%–90% combined humic and fulvic acids. Typically, leonardite is a low-rank coal derived from terrestrial plant matter, usually found in conjunction with deposits of lignite. It was discovered in 1919 in North Dakota and has been subsequently found in Utah and New Mexico. Usually, leonardite is found as an outcropping of lignite deposits often located close to the surface of the earth.

The origin of leonardite and humic shales is mainly beds of vegetation, though animal life has contributed somewhat to the result. The beds were once beds of vegetation, analogous, in most respects, in mode of formation to the peat beds of modem time, yet in modes of burial often of a very different character. The deposits existed millions of years ago when lush vegetation was abundant. The deposits in some cases were covered by volcanic eruptions, covering the vegetation with a layer of mud and ash to create an "encasement" which prevented the deposit from fossilizing, petrifying, or turning into coal. Water was essentially excluded from the deposit preventing fossilization. These deposits are commonly known as Humus or Organic clays or shales or brown coal.

Humate is characterized as humic matter, which is complex organic molecules formed by the breakdown of organic matter. Humic matter is a class of compounds having variable structure, functionalities and reactivities. Typically, three types of organics, fulvic acid, humic acid and humin, are identified in leonardite and humus shales. The fulvic acid is the acid radical found in the humic matter, which is soluble in alkali and acids. Humic acid is the acid radical found in the humic-humus matter, which is soluble in alkali but insoluble in acid. Humin is the insoluble fraction of humates which is insoluble in both acidic and alkaline solutions.

Leonardite and humus shales have both industrial as well as agricultural uses. In agriculture, leonardite is used as soil amendments and fertilizer. For waste water treatment, metals and organics are filtered using leonardite. Leonardite is also an additive in drilling mud used for drilling oil. For foundry applications, leonardite is an additive to green sand.

Leonardite is commonly known as a source for humic acids. Extraction methods and applications of the humic acids extracted from leonardite are also well known. The extraction methods are based on humic acid and fulvic acid being soluble in alkali, but only fulvic acid being soluble in acid. Several definitions of terms used herein as follows:

Humus is the product of the decay of organic matter and contains both humic and non-humic material.

Humic matter is completely decomposed organic matter, and is readily soluble either in acids or bases.

Humic acids is the collective name for the acid radicals found in humic matter, they may be separated from humic matter by alkaline extraction.

Humates are the salts of humic acids, collectively, of the salts of humic acids specifically.

Fulvic acid is the acid radical found in humic matter which is soluble in alkali, acid, and various alcohols.

Fulvates are the salts of fulvic acid.

OBJECT AND SUMMARY OF THE INVENTION

It is an object of the invention to provide a method for producing magnesium fulvate from humus material such as naturally-occurring leonardite and humus shales.

Accordingly, a method of the invention for producing magnesium fulvate from naturally-occurring humus material is hereinafter described. The method of the invention includes the step of mixing the humus material, which contains fulvic acid, humic acid and humin, with water and sodium hydroxide to form a solution having a first alkaline pH. Amounts of the humus material, water and sodium hydroxide are mixed in respective quantities sufficient to solublize the fulvic acid and the humic acid while the humin remains insoluble. Another step is precipitating the humic acid as a solid while maintaining the solubilized fulvic acid in solution. Another step is separating the solid humic acid and the solubilized fulvic acid. Another step is adding an amount of magnesium hydroxide to the solubilized fulvic acid which is sufficient to precipitate the solubilized fulvic acid as magnesium fulvate.

Other objects and advantages of the invention will become apparent from the following description of the invention taken in conjunction with the accompanying drawing.

BRIEF DESCRIPTION OF THE DRAWING

FIG. 1 is a diagrammatic flow chart of a system for implementing a method for producing magnesium fulvate from humus material.

DETAILED DESCRIPTION OF THE INVENTION

A method for producing magnesium fulvate from humus material uses equipment and the arrangement thereof illustrating FIG. 1. However, one of ordinary skill in the art would appreciate that the equipment and arrangement thereof are used by way of example only and that other equipment and other arrangements thereof can be used to practice the method of the invention.

In FIG. 1, a humus material 2 is conveyed to an impact mill 4. The humus material 2 typically contains fulvic acid, humic acid and humin which are in a solid state. The humus material 2 is dry grounded preferably to a powdered form. Although not by way of limitation, the powdered humus material 2 is sized in a range approximately between 50 and 100 mesh.

The powdered humus material 2 is conveyed from the impact mill 4 to a first mixing tank 6. The powdered humus material 2 is mixed with water 8 in the first mixing tank 6. Mixing the humus material 2 and water forms a mixture containing approximately 3.25% solids, i.e., 57 grams per liter. Sodium hydroxide 10 is added to the mixture of humus material 6 and water 8 to form a solution having a first alkaline pH. Preferably, the first alkaline pH is approximately 10.0. However, the humus material 2, water 8 and sodium hydroxide 10 are mixed in respective quantities sufficient to solubilize the fulvic acid and the humic acid while the humin remains insoluble. The solution having the first alkaline pH is mixed for at least 15 minutes although, preferably, the solution is mixed for approximately 30 minutes.

After the solution is mixed for a first selected time period, i.e., at least 15 minutes, the solution is transferred to a second mixing tank 12. In the second mixing tank, the humic acid is precipitated as solid while maintaining the solubilized fulvic acid in solution. Such precipitation requires adjusting the first alkali pH to an acidic pH. Although not by way of limitation, the first alkaline pH is adjusted to the acidic pH of approximately 4.5. Preferably, adjusting the first alkaline pH to the acidic pH is achieved by adding an appropriate amount of hydrochloric acid 14 to the solution. The solution, now having the acidic pH, is mixed for a second selected time period of at least 15 minutes. Preferably, the second selected time period is approximately 30 minutes.

At an approximate pH of 4.5, the bulk of the humic acids are precipitated as insoluble humates, and is so doing rid the solution of extraneous metal ions which have been leached from the clay minerals. Only those minerals naturally chelated with the fulvic acid remain in solution. The insoluble humic acids report with the insoluble humin. The fulvic acids remain in solution, thus effecting separation of the humic acid and the fulvic acid.

Upon expiration of the second selected time period, the solution in the second mixing tank 12 is passed through a static mixer 14. Preferably, a polymer 16 is added to the solution as it passes through the static mixer 14, to assist in settling the humic acid flocks. The polymer 16 causes the insoluble fraction to coagulate into large flocks leaving a clarified solution. While the fulvic acid remains soluble in solution, the polymer 16 is added as a coagulating agent.

The polymerized solution is transferred to a thickener tank 18. The polymerized solution is allowed to settle in the thickener tank 18 for a third selected period of time to effect a solids/liquid separation. Preferably, the third selected time period is approximately 1 hour. The flocculents, i.e., the insoluble humic acid fraction, settles to a bottom of the thickener tank 18 to accumulate the flocculents. The accumulated flocculents are transported to a filter 20 where the solids are removed and washed. Filtrate solution 22 generated from washing of the flocculents is recycled to the first mixing tank 6 by a conduit 24. Overflow solution from a thickener tank 18 is conveyed to a precipitation tank 26. The overflow solution contains the solubilized fulvic acid. An amount of magnesium hydroxide 28 is added to the overflow solution, i.e., the fulvic acid solution, which is sufficient to precipitate the solubilized fulvic acid as magnesium fulvate 30, which is insoluble.

The solution from the precipitation tank 26 which now contains the precipitated magnesium fulvate 30 is directed to a filter 32. Such as a plate and frame filter illustrated in FIG. 1. The magnesium fulvate 30 is separated from waste solution 34, which is discarded. The magnesium fulvate 30 is retained by the filter 32 and is washed with water and partially dried in the filter 32 prior to discharge.

Although the invention has been specifically described herein, it will be apparent to those skilled in the art to which the invention pertains that other variations and modifications of the embodiment shown and described herein may be made without departing from the spirit and scope of the invention.

Adding the magnesium hydroxide causes the acidic pH to change to a second alkaline pH. Preferably, the second alkaline pH is approximately 10.5.

The magnesium fulvate is separated from the remaining solution. Preferably, separation of the magnesium fulvate from the remaining solution is achieved by filtering. Thus, magnesium fulvate in produced from human material.

Although the invention has been specifically described herein, it would be apparent to those skilled in the art to which the invention pertains that other variations and modifications of practicing the invention may be made without departing from the spirit and scope of the invention.

What is claimed is:

1. A method for producing magnesium fulvate from humus material, comprising the steps of:

mixing the humus material containing fulvic acid, humic acid and humin with water and sodium hydroxide to form a solution having a first alkaline pH, the humus material, water and sodium hydroxide being mixed in respective quantities sufficient to solubilize the fulvic acid and the humic acid while the humin remains insoluble;

precipitating the humic acid as a solid while maintaining the solubilized fulvic acid in solution;

separating the solid humic acid and the fulvic acid solution; and adding an amount of magnesium hydroxide to the fulvic acid solution sufficient to precipitate the solubilized fulvic acid as magnesium fulvate.

2. A method according to claim 1, wherein the mixing step includes a step of mixing forms a mixture of humus material and water containing approximately 3.25% solids.

3. A method according to claim 1, wherein the mixing step results in the solution having the first alkaline pH as approximately 10.0.

4. A method according to claim 1, wherein the solution having the first alkaline pH is mixed for at least 15 minutes.

5. A method according to claim 1, wherein the precipitating step includes adjusting the first alkaline pH to an acidic pH.

6. A method according to claim 5, wherein the acidic pH is approximately 4.5.

7. A method according to claim 5, wherein adjusting the first alkaline pH to the acidic pH is achieved by adding hydrochloric acid to the solution.

8. A method according to claim 5, wherein the solution having the acidic pH is mixed for at least 15 minutes.

9. A method according to claim 1, further comprising the step of adding a coagulating agent after the precipitating step.

10. A method according to claim 9, wherein the coagulating agent is a non-ionic polymer.

11. A method according to claim 1, wherein the separating step includes thickening.

12. A method according to claim 1, the adding step causes the acidic pH to change to a second alkaline pH.

13. A method according to claim 12, wherein the second alkaline pH is approximately 10.5.

14. A method according to claim 1, further comprising the step of separating the magnesium fulvate from a remaining solution.

15. A method according to claim 14, wherein the separating step includes filtering after a sufficient residence time.

16. A method according to claim 1, wherein the humus material is in a form of a powder.

17. A method according to claim 16, wherein the powered humus material is sized in a range approximately between 60 and 100 mesh.

18. A method according to claim 1, wherein the humus material in at least one of the leonardite and humus shale.

19. A method for producing magnesium fulvate from humus material, comprising the steps of:

mixing the humus material containing solid fulvic acid and solid humic acid with water and sodium hyroxide for a first selected time period to form a solution having a pH of approximately 10.0 thereby solubilizing the fulvic acid and the humic acid;

reducing the pH of the solution to approximately 4.5;

maintaining the solution at the approximate pH 4.5 for a second selected time period thereby precipitating the humic acid as a solid while the fulvic acid remains in solution;

separating the fulvic acid solution and the solid humic acid; and increasing the pH of the fulvic acid solution to approximately 10.5 with magnesium hydroxide thereby precipitating the solubilized fulvic acid as magnesium fulvate.

20. A method according to claim 19, wherein the humus is in a form of a powder.

21. A method according to claim 19, wherein the mixing step includes mixing humus material and water to form a mixture containing approximately 3.25% solids.

22. A method according to claim 19, wherein the first selected time period is at least 15 minutes.

23. A method according to claim 19, wherein the second selected time period is at least 15 minutes.

24. A method according to claim 19, wherein the reducing step is achieved by adding hydrochloric acid.

25. A method according to claim 19, wherein the humus material in at least one of leonardite and humus shale.

* * * * *